United States Patent
Högberg et al.

(10) Patent No.: US 8,173,027 B2
(45) Date of Patent: May 8, 2012

(54) METHOD OF SEPARATING A COMPOSITE LIQUID INTO AT LEAST TWO COMPONENTS

(75) Inventors: Niclas Högberg, Golden, CO (US);
Brian M. Holmes, Lakewood, CO (US);
Briden Ray Stanton, Highlands Ranch, CO (US); Lars Persson, Karlskoga (SE);
Lars Strandberg, Gävle (SE); Peter Pihlstedt, Stockholm (SE)

(73) Assignee: Terumo BCT, Inc., Lakewood, CO (US)

( * ) Notice: Subject to any disclaimer, the term of this patent is extended or adjusted under 35 U.S.C. 154(b) by 593 days.

(21) Appl. No.: 11/845,971

(22) Filed: Aug. 28, 2007

(65) Prior Publication Data

US 2008/0053203 A1 Mar. 6, 2008

Related U.S. Application Data

(60) Provisional application No. 60/824,643, filed on Sep. 6, 2006.

(51) Int. Cl.
*B01D 21/26* (2006.01)
*B04B 15/00* (2006.01)
*A61B 19/00* (2006.01)

(52) U.S. Cl. ......... 210/782; 210/787; 210/88; 210/109; 210/117; 210/929; 494/37; 494/27; 494/45; 494/10; 604/407; 604/410

(58) Field of Classification Search .................... 494/10, 494/27–30, 37, 45; 210/781, 782, 787, 85–88, 210/97, 104, 109, 112, 117, 143, 360.1, 378, 210/380.1, 382, 361, 929; 422/72; 604/4.01, 604/6.01, 6.15, 407, 408, 410
See application file for complete search history.

(56) References Cited

U.S. PATENT DOCUMENTS

| | | | |
|---|---|---|---|
| 3,297,244 A | 1/1967 | Hein | |
| 3,326,458 A | 6/1967 | Merman et al. | |
| 3,679,128 A | 7/1972 | Unger et al. | |
| 3,708,110 A | 1/1973 | Unger et al. | |

(Continued)

FOREIGN PATENT DOCUMENTS

EP 0499891 8/1992

(Continued)

OTHER PUBLICATIONS

PCT/US2007/076987, "Invitation to Pay Additional Fees", mailed Feb. 11, 2008.

(Continued)

*Primary Examiner* — Tony G Soohoo
*Assistant Examiner* — David C Mellon
(74) *Attorney, Agent, or Firm* — Elizabeth J. Reagan; Edna M O'Connor; John R. Merkling

(57) ABSTRACT

Method for separating a volume of composite liquid into at least a first component and a second component including centrifuging a separation bag containing a volume of composite liquid and a volume of gas so as to sediment at least a first component and a second component separation bag; displacing a volume of hydraulic fluid against the separation bag to cause a transfer of at least one fraction of the content of the separation bag into at least one component bag connected to the separation bag; determining the volume of hydraulic fluid displaced and determining the volume of the composite liquid or the transferred components from the determined volume of displaced hydraulic fluid.

13 Claims, 4 Drawing Sheets

U.S. PATENT DOCUMENTS

| | | | |
|---|---|---|---|
| 3,724,747 A | 4/1973 | Unger et al. | |
| 3,737,096 A | 6/1973 | Jones et al. | |
| 3,858,796 A | 1/1975 | Unger et al. | |
| 3,987,961 A | 10/1976 | Sinn et al. | |
| 4,007,871 A * | 2/1977 | Jones et al. | 494/45 |
| 4,146,172 A | 3/1979 | Cullis et al. | |
| 4,389,207 A | 6/1983 | Bacehowski et al. | |
| 4,405,079 A | 9/1983 | Schoendorfer | |
| 4,417,884 A * | 11/1983 | Schoendorfer et al. | 494/4 |
| 4,421,503 A | 12/1983 | Latham, Jr. et al. | |
| 4,482,342 A | 11/1984 | Lueptow et al. | |
| 4,720,284 A | 1/1988 | McCarty | |
| 4,850,995 A | 7/1989 | Tie et al. | |
| 4,990,132 A | 2/1991 | Unger et al. | |
| 5,114,396 A | 5/1992 | Unger et al. | |
| 5,427,695 A | 6/1995 | Brown | |
| 5,543,062 A | 8/1996 | Nishimura | |
| 5,632,906 A | 5/1997 | Ishida et al. | |
| 5,637,082 A | 6/1997 | Pages et al. | |
| 5,723,050 A | 3/1998 | Unger et al. | |
| 5,738,644 A | 4/1998 | Holmes et al. | |
| 5,874,208 A | 2/1999 | Unger | |
| 5,904,355 A | 5/1999 | Powers et al. | |
| 5,964,724 A | 10/1999 | Rivera et al. | |
| 6,039,711 A | 3/2000 | Headley et al. | |
| 6,261,217 B1 | 7/2001 | Unger et al. | |
| 6,296,602 B1 | 10/2001 | Headley | |
| 6,315,706 B1 | 11/2001 | Unger et al. | |
| 6,348,031 B1 | 2/2002 | Unger et al. | |
| 6,439,577 B2 | 8/2002 | Jorgensen et al. | |
| 6,656,105 B2 | 12/2003 | Hogberg et al. | |
| 2002/0068674 A1 * | 6/2002 | Hlavinka et al. | 494/37 |
| 2002/0068675 A1 * | 6/2002 | Felt et al. | 494/37 |
| 2002/0119880 A1 | 8/2002 | Hogberg et al. | |
| 2004/0026341 A1 | 2/2004 | Hogberg et al. | |

FOREIGN PATENT DOCUMENTS

| | | |
|---|---|---|
| EP | 0771569 | 5/1997 |
| EP | 1566191 | 8/2005 |
| WO | WO92/00145 | 1/1992 |
| WO | WO01/02037 | 1/2001 |
| WO | WO01/97943 | 12/2001 |
| WO | WO03/089027 | 10/2003 |
| WO | WO03/090839 | 11/2003 |
| WO | WO2004/018021 | 3/2004 |

OTHER PUBLICATIONS

International Search Report for PCT/US2007/076987, mailed Apr. 23, 2008.

* cited by examiner

METHOD OF SEPARATING A COMPOSITE LIQUID INTO AT LEAST TWO COMPONENTS

CROSS REFERENCE TO RELATED APPLICATIONS

This application claims the benefit of U.S. Provisional Application No. 60/824,643 filed Sep. 6, 2006.

FIELD OF THE INVENTION

The present invention concerns an apparatus and a method for separating a volume of composite liquid into at least two components.

The apparatus and method of the invention are particularly appropriate for the separation of biological fluids comprising an aqueous component and one or more cellular components. For example, potential uses of the invention include extracting, from a volume of whole blood, a plasma component, a first cellular component including platelets, a second cellular component including mononuclear cells, and a third cellular component including red blood cells and granulocytes.

DESCRIPTION OF RELATED ART

European patent application EP 1 566 191 describes a method and an apparatus for separating a volume of whole blood into at least two components in accordance with various separation protocols. For example, one protocol provides for the separation of a volume of whole blood into a plasma component, a platelet component, and a red blood cell component. The apparatus comprises a centrifuge adapted to cooperate with various bag sets, in particular a bag set comprising an annular separation bag for whole blood, which is connected to a platelet component bag, a plasma component bag, and a red blood cell component bag.

The centrifuge includes a rotor for spinning the separation bag and centrifuging the whole blood contained therein, the rotor having a turntable for supporting the separation bag and a central compartment for containing the component bags connected to the separation bag and a squeezing system for squeezing the separation bag and causing the transfer of the plasma component from the separation bag into the plasma component bag, of the red blood cell component into the red blood cell component bag and, as the case may be, of the platelet component into the platelet component bag.

SUMMARY OF THE INVENTION

An object of the invention is to design a separation apparatus that can perform an optimized separation process for separating, in a minimum period of time, a composite fluid into at least two high quality components.

According to a first embodiment of the invention, a method for separating a volume of composite liquid into at least a first component and a second component comprises centrifuging a separation bag containing a volume of composite liquid so as to cause the sedimentation of at least a first component and a second component in the separation bag, wherein a volume of gas is present in the separation bag; displacing a volume of hydraulic fluid against the separation bag so as to apply a pressure onto the separation bag and cause a transfer of at least one fraction of a content of the separation bag into at least one component bag connected to the separation bag; determining a volume of hydraulic fluid being displaced so as to cause the transfer of at least one fraction of a content of the separation bag into at least one component bag; determining, from the determined volume of displaced hydraulic fluid, at least one of an actual volume of the composite liquid in the separation bag, an actual volume of the second component in the separation bag, and an actual volume of at least one fraction of the first component transferred into a first component bag.

Additional or alternative characteristics of this method are as follows. Applying a pressure on the separation bag so as to cause the transfer of at least one fraction of the content of the separation bag into at least one component bag comprises causing a residual volume of gas and the first component to flow into the first component bag; and stopping a flow of the first component into the first component bag when at least a first fraction thereof has been transferred into the first component bag.

The method further comprises determining when the first fraction of the first component starts pouring into the first component bag after the residual volume of gas has been transferred therein, wherein the actual volume of the first fraction of the first component transferred into the first component bag substantially corresponds to the volume being transferred between the first component starting pouring into the first component bag and the first component stopping flowing into the first component bag.

Determining when the first fraction of the first component starts pouring into the first component bag comprises monitoring an evolution of the pressure applied onto the separation bag and determining from a change in pressure applied onto the separation bag when the first fraction of the first component starts pouring into the first component bag.

The change in pressure corresponds to the pressure becoming substantially constant after having been substantially steadily raised during the transfer of gas into the first component bag.

Applying a pressure onto the separation bag comprises pumping a hydraulic liquid in a separation compartment in which the separation bag is enclosed.

Monitoring an evolution of a pressure applied onto the separation bag comprises measuring the pressure of the hydraulic liquid.

Pumping the hydraulic liquid into the separation compartment comprises pumping the hydraulic liquid in increments of a determined discrete volume, and determining the actual volume of the first fraction of the first component transferred into the first component bag comprises counting the number of increments between the first component starting pouring into the first component bag and the first component stopping flowing into the first component bag.

The method further comprises detecting an interface between the first and second component in the separation bag at a distance from a centrifugation axis, wherein the flow of the first component into the first component bag is stopped after the interface is detected.

Determining the actual volume of composite liquid in the separation bag comprises displacing a volume of hydraulic fluid against the separation bag so as to cause a transfer of the volume of gas contained in the separation bag into at least one component bag and the first fraction of the first component to pour into the first component bag, wherein the separation bag is enclosed in a separation compartment having a fixed volume determining the volume of displaced hydraulic fluid until the first fraction of the first component starts pouring into the first component bag; and determining the actual volume of composite liquid in the separation bag from at least the fixed volume of the separation compartment and the determined volume of displaced hydraulic fluid until the first fraction of the first component starts pouring into the first component bag.

Displacing the volume of hydraulic fluid against the separation bag comprises pumping the hydraulic fluid, in increments of a determined discrete volume, in the separation compartment in which the separation bag is enclosed; and determining the actual volume of composite liquid in the separation bag comprises counting the number of increments between the hydraulic fluid starting flowing in the separation compartment and the first fraction of the first component starting pouring into the first component bag.

The method further comprises determining an actual volume of the second component in the separation bag from at least the determined actual volume of the composite liquid in the separation bag, and the determined actual volume of the first component transferred into the first component bag.

Centrifuging the separation bag causes the sedimentation of an intermediate component between the first component and the second component in the separation bag.

The method further comprises causing a third component to flow into a third component bag connected to the separation bag when a first fraction of the first component has been transferred into the first component bag, wherein the third component comprises a fraction of the second component, the intermediate component, and a second fraction of the first component remaining in the separation bag when the first fraction of the first component has been transferred into the first component bag; stopping a flow of the third component into the third component bag when a volume thereof has been transferred into the third component bag; and determining an actual volume of the third component transferred into the third component bag.

The method further comprises initially transferring the volume of composite liquid into the separation bag from a composite liquid bag connected to the separation bag, wherein a residual volume of composite liquid remains in the composite liquid bag, and wherein the residual volume has a known value; using the composite liquid bag as the third component bag; and determining an actual volume of the third component in the composite liquid bag from at least the residual volume of composite liquid and the actual volume of third component transferred into the composite liquid bag.

Causing the third component to flow into the composite liquid bag comprises pumping, in increments of a determined discrete volume, a hydraulic liquid into a separation compartment containing the separation bag.

Determining an actual volume of the third component transferred into the composite liquid bag comprises counting the increments between the third component starting flowing into the third component bag and the third component stopping flowing into the third component bag, and calculating the actual volume of the third component transferred into the composite liquid bag from the counted number of increments and the determined volume of one increment.

The method further comprises determining the actual volume of composite liquid in the separation bag; and determining an actual volume of the second component from at least the determined actual volume of the composite liquid, a determined actual volume of the first component transferred into the first component bag, and the determined actual volume of the third component transferred into the third component bag.

In one embodiment of the invention the composite liquid comprises whole blood, the first component comprises plasma, the second component comprises red blood cells and the intermediate component comprises platelets.

According to a second embodiment of the invention, a method for separating a volume of composite liquid into at least a first component and a second component, comprises centrifuging a separation bag containing a volume of composite liquid so as to cause the sedimentation of at least a first component and a second component in the separation bag, wherein a residual volume of gas is present in the separation bag; causing the residual volume of gas and the first component to flow into a first component bag connected to the separation bag; stopping a flow of the first component into the first component bag when at least a first fraction thereof has been transferred into the first component bag; determining when the first fraction of the first component starts pouring into the first component bag after the residual volume of gas has been transferred therein; determining an actual volume of the first fraction of the first component transferred into the first component bag, wherein the actual volume of the first fraction of the first component substantially corresponds to the volume being transferred between the first component starting pouring into the first component bag and the first component stopping flowing into the first component bag.

According to a third embodiment of the invention, a method for separating a volume of composite liquid into at least a first component and a second component, comprises centrifuging a separation bag containing a volume of composite liquid so as to cause the sedimentation of at least a first component and a second component in the separation bag, wherein a volume of gas is present in the separation bag; pumping a hydraulic fluid in a separation compartment in which the separation bag is enclosed so as to cause a transfer of the volume of gas contained in the separation bag into at least one component bag connected to the separation bag and the transfer of a first fraction of the first component into a first component bag connected to the separation bag, wherein the separation compartment has a fixed volume; determining a volume of hydraulic fluid pumped into the separation compartment until the first fraction of the first component starts pouring into the first component bag; and determining the actual volume of composite liquid in the separation bag from at least the fixed volume of the separation compartment, and the volume of hydraulic fluid pumped into the separation compartment until the first fraction of the first component starts pouring into the first component bag.

According to a fourth embodiment of the invention, a method for separating a volume of composite liquid into at least a first component and a second component, comprises centrifuging a separation bag containing a volume of composite liquid so as to cause the sedimentation of at least a first component and a second component in the separation bag, wherein a residual volume of gas is present in the separation bag; determining an actual volume of composite liquid in the separation bag; causing at least a first fraction of the first component to flow into a first component bag connected to the separation bag; determining an actual volume of the at least first fraction of the first component transferred into the first component bag; and determining an actual volume of the second component in the separation bag from at least the actual volume of composite liquid and the actual volume of the first fraction of the first component.

According to a fifth embodiment of the invention, a method for separating a volume of composite liquid into at least a first component, a second component, and an intermediate component, comprises centrifuging a separation bag containing a volume of composite liquid so as to cause the sedimentation of at least a first component, a second component, and an intermediate component in the separation bag; causing the first component to flow into a first component bag connected to the separation bag; detecting an interface between the first and intermediate component in the separation bag at a distance from a centrifugation axis; stopping a flow of the first component into the first component bag after the interface is detected; causing a third component to flow into a third component bag connected to the separation bag, when the first fraction of the first component has been transferred into the first component bag, wherein the third component comprises a fraction of the second component, the intermediate component, and a second fraction of the first component remaining in the separation bag when the first fraction of the first component has been transferred into the first component bag; stopping a flow of the third component into the third component bag when a volume thereof has been transferred into the third component bag; and determining an actual volume of the third component in the third component bag.

According to the invention, an apparatus for separating a volume of composite liquid into at least a first component and a second component comprises a rotor for spinning a separation bag around a rotation axis of the rotor; a fluid transfer system for causing a transfer of gas and at least a first fraction of a first component from a separation bag into a first component bag connected thereto; a memory for storing at least one centrifugation speed allowing for the sedimentation of at least a first component and a second component of a volume of composite liquid contained in a separation bag; and a control unit programmed for causing the rotor to rotate at the at least one centrifugation speed so as to cause the sedimentation of at least a first and second component of a volume of composite liquid contained in a separation bag, for causing the fluid transfer system to transfer gas and at least a fraction of the first component into a first component bag connected to the separation bag, and for determining an actual volume of the at least one fraction of the first component transferred into a first component bag, between the first component starting pouring into the first component bag and the first component stopping flowing into the first component bag.

Additional or alternative characteristics of this apparatus are as follows. The fluid transfer system comprises a means for applying a pressure onto a separation bag; and a pressure sensor for measuring a pressure applied to the separation bag, wherein the control unit is further programmed for receiving information from the pressure sensor, and for monitoring the pressure information from the pressure sensor so as to determine when the first fraction of the first component actually starts pouring into the first component bag after a volume of gas has been transferred therein.

The control unit is further programmed for determining when the first fraction of the first component actually starts pouring into the first component bag by detecting a change in pressure corresponding to the pressure becoming substantially constant after having substantially steadily raised during the transfer of the volume of gas.

The apparatus further comprises an interface sensor for detecting an interface between the; first and second component in the separation bag at a distance from the rotation axis, and the control unit is further programmed for receiving information from the interface sensor, and for causing the fluid transfer system to stop transferring the first component into the first component bag after the interface between the first and second component is detected by the interface sensor.

The fluid transfer system comprises a pumping means for pumping a hydraulic liquid, in increments of a determined discrete volume, into a separation compartment of the rotor for containing the separation bag; and the control unit is further programmed for counting the number of increments between the first component starting pouring into the first component bag and the first component stopping flowing into the first component bag, and for determining the actual volume of the first fraction of the first component transferred into the first component bag from the counted number of increments and the determined volume corresponding to one increment.

The apparatus further comprises an interface sensor for detecting an interface between gas and the composite liquid in the separation bag at a distance from the rotation axis, and the control unit is further programmed for receiving information from the interface sensor, and for causing the fluid transfer system to transfer gas from the separation bag into a satellite bag connected thereto until a determined period of time has lapsed after an interface between gas and the composite liquid is detected by the interface sensor.

The fluid transfer system comprises a pumping means for pumping a hydraulic liquid into a separation compartment of the rotor for containing the separation bag, wherein the separation compartment has a fixed volume; and the control unit is further programmed for pumping a hydraulic fluid into the separation compartment so as to cause a transfer of a volume of gas contained in the separation bag into at least one component bag and the transfer of the first fraction of the first component into the first component bag, for determining a volume of hydraulic fluid pumped into the separation compartment until the first fraction of the first component starts pouring into the first component bag, and determining the actual volume of composite liquid in the separation bag from at least the fixed volume of the separation compartment and the volume of hydraulic fluid pumped into the separation compartment until the first fraction of the first component starts pouring into the first component bag.

The pumping means is designed for pumping the hydraulic fluid in increments of a determined discrete volume, and the control unit is further programmed for counting the number of increments between the hydraulic fluid starting flowing into the separation compartment and the first fraction of the first component starting pouring into the first component bag, and for calculating the volume of hydraulic fluid pumped into the separation compartment from the counted number of increments and the determined discrete volume of one increment.

The control unit is further programmed for determining an actual volume of the second component from at least the determined actual volume of the composite liquid in the separation bag, and the actual volume of the first component transferred into the first component bag.

One of the at least one centrifugation speed stored in the memory allows for the sedimentation of at least a first component, a second component, and an intermediate component of a volume of composite liquid contained in a separation bag, and the control unit is further programmed for causing the rotor to rotate at the centrifugation speed allowing for the sedimentation of a first, second and intermediate components of a volume of composite liquid contained in a separation bag; causing the fluid transfer system to transfer a volume of a third component into a third component bag connected to the separation bag, when the first fraction of the first component has been transferred into the first component bag, wherein the third component comprises a fraction of the second component, the intermediate component, and a second fraction of the first component remaining in the separation bag when the first fraction of the first component has been transferred into the first component bag; and determining an actual volume of the third component transferred into the third component bag.

The fluid transfer system comprises a pumping means for pumping a hydraulic fluid and the control unit is further programmed for counting the number of increments between the pumping means being actuated to transfer the third component into the third component bag and the pumping means being stopped; and determining the actual volume of the third component transferred into the third component bag from the counted number of increments and the determined volume of one increment.

The control unit is further programmed for determining an actual volume of the second component from at least an actual volume of the composite liquid, the determined actual volume of the first component transferred into the first component bag, and the determined actual volume of the third component transferred into the third component bag.

The apparatus further comprises a screen connected to the control unit, and the control unit is further programmed for displaying on the screen at least one of the actual volume of the composite liquid in the separation bag, the actual volume of the second component in the separation bag, the actual volume of the at least one fraction of the first component transferred into the first component bag, and the actual volume of the third component transferred into the third component bag.

BRIEF DESCRIPTION OF DRAWINGS

Other features and advantages of the invention will appear from the following description and accompanying drawings, which are to be considered exemplary only.

In the accompanying drawings.

DETAILED DESCRIPTION

For the sake of clarity, the invention will be described with respect to a specific use, namely the separation of whole blood into four components, namely a plasma component, a platelet component, a mononuclear cell component, and a red blood cell component. It should be understood however that this specific use is exemplary only.

Figure 1:
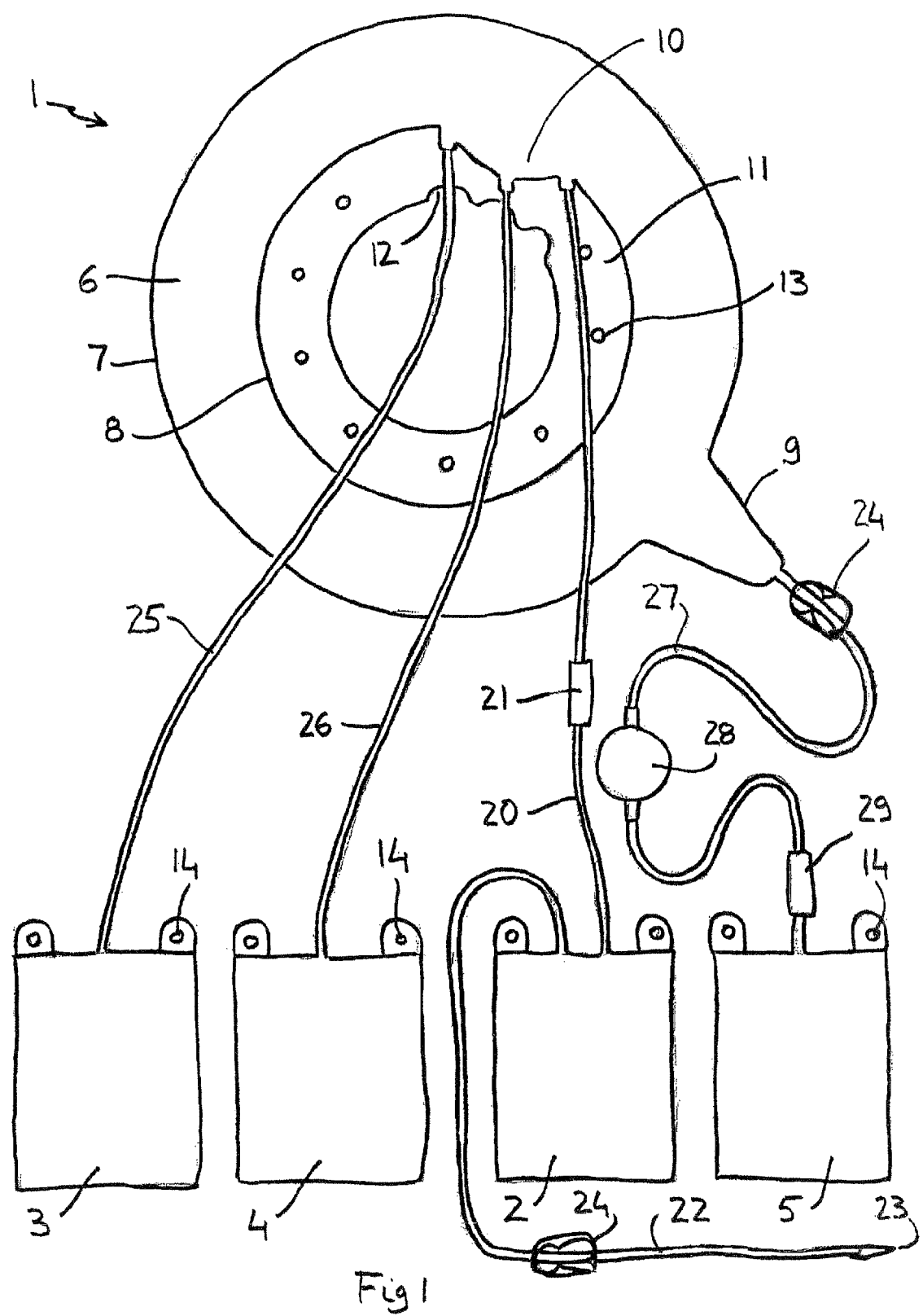
FIG. 1 is a schematic view of a set of bags designed for cooperating with a separation apparatus according to the invention.
Figure 2:
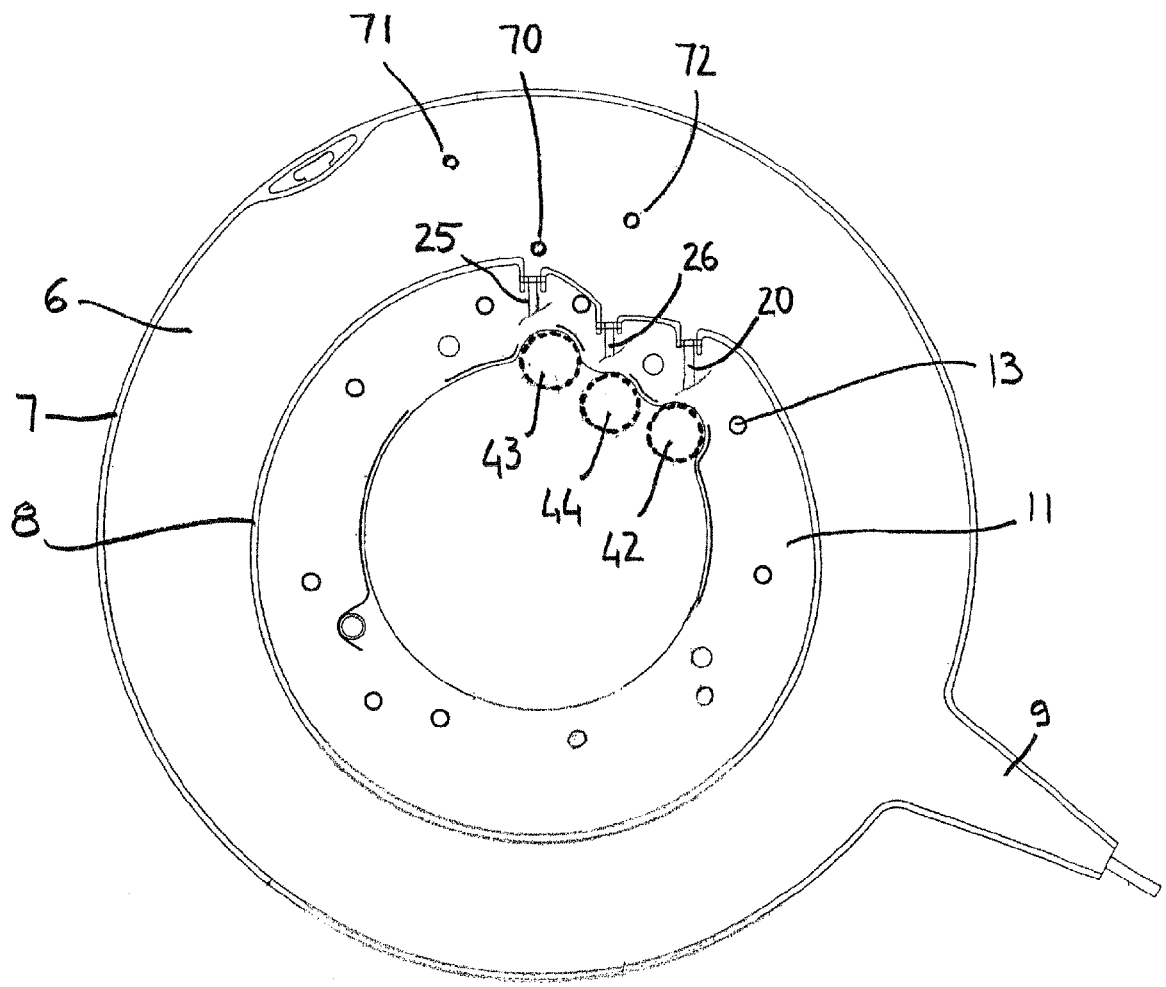
FIG. 2 is an enlarged view of the separation bag of the set of bags of FIG. 1.

FIGS. 1 and 2 show an example of a set of bags adapted to the separation of whole blood into a plasma component (essentially comprising plasma), a platelet component (essentially comprising platelets), a mononuclear cell component (comprising monocytes, lymphocytes and red blood cells) and a red blood cell component (essentially comprising red blood cells and granulocytes). This bag set comprises a flexible separation bag 1 and four flexible satellite bags 2, 3, 4, 5 connected thereto. The separation bag 1 comprises an annular separation chamber 6 having generally circular outer and inner edges 7, 8. The outer circular edge 7 and the inner circular edge 8 of the separation chamber 6 are substantially concentric.

The separation chamber 6 comprises a first, acute-angled, funnel-like extension 9 protruding outwardly from its outer edge 7 for helping drain a content of the separation chamber 6 into the fourth satellite bag 5. The separation chamber 6 also comprises a second, obtuse-angled, funnel-like extension 10 protruding from the inner edge 8, towards the center of the bag 1, for helping funnel separated components into the first, second and third satellite bags 2, 3, 4.

The separation bag 1 further comprises a semi-flexible disk-shaped connecting element 11 that is connected to the inner edge 8 of the annular chamber 5. The disk-shaped connecting element 11 comprises three rounded recesses 12 on its inner edge facing the second funnel-like extension 10, for partially surrounding three pinch valve members of a rotor of a centrifuge to be described later (diagrammatically shown in doted line in FIG. 2). The disk-shaped connecting element 11 comprises a series of holes 13 for connecting the separation bag 1 to the rotor of a centrifuge.

The first satellite bag 2 has two purposes, and is successively used as a whole blood collection bag and as a mononuclear cell component bag. The first satellite bag 2 is intended for initially receiving a volume of whole blood from a donor (usually about 450 ml) before the separation process, and the mononuclear cell component during the separation process. The first satellite bag 2 is flat, substantially rectangular, and comprises two reinforced ears at its upper corners having holes 14 for hanging the bag. It is connected to the separation bag 1 by a first transfer tube 20 having a first end connected to the upper edge of the first satellite bag 2 and a second end connected to the second funnel-like extension 10, close to the inner circular edge 8. The first satellite bag 2 contains a volume of anti-coagulant solution (typically about 63 ml of a solution of citrate phosphate dextrose for a blood donation of about 450 ml). A frangible connector 21 mounted on the transfer tube 20 blocks a liquid flow through the first transfer tube 20 and prevents the anti-coagulant solution from flowing from the first satellite bag 2 into the separation bag 1.

The bag set further comprises a collection tube 22 that is connected at one end to the upper edge of the first satellite bag 2 and comprises, at the other end, a needle protected by a sheath 23. The collection tube 22 is fitted with a clamp 24.

The second satellite bag 3 is intended for receiving a plasma component. The second satellite bag 3 is flat, substantially rectangular, and comprises two reinforced ears at its upper corners having holes 14 for hanging the bag. It is connected by a second transfer tube 25 to the separation bag 1. The second transfer tube 25 has a first end connected to the upper edge of the second satellite bag 3 and a second end connected to the second funnel-like extension 10, close to the inner circular edge 8, opposite the second end of the first transfer tube 20 with respect to the tip of the second funnel-like extension 10.

The third satellite bag 4 is intended for receiving a platelet component. It is flat, substantially rectangular, and comprises two reinforced ears at its upper corners having holes 14 for hanging the bag. It is connected by a third transfer tube 26 to the separation bag 1. The third transfer tube 26 has a first end connected to the upper edge of the third satellite bag 4 and a second end connected to the tip of the second funnel-like extension 10.

The fourth satellite bag 5 is intended for receiving a red blood cell component. It is flat, substantially rectangular, and comprises two reinforced ears at its upper corners having holes 14 for hanging the bag. It is connected by a fourth transfer tube 27 to the separation bag 1. The fourth transfer tube 27 has a first end connected to the upper edge of the fourth satellite bag 5 and a second end connected to the tip of the first funnel-like extension 9. It comprises two tube segments respectively connected to the inlet and the outlet of a leuko-reduction filter 28. The tube segment connected to the separation bag 1 is fitted with a clamp 24. The tube segment connected to the fourth satellite bag 5 is fitted with a frangible connector 29, which, when broken, allows a flow of liquid between the separation bag 1 and the fourth satellite bag 5. The filter may be, for example, a filter of the type RC2D manufactured by Pall Corporation. Such a filter comprises a disk-shaped casing to which radial inlet and outlet ports are connected, in diametral opposition. The casing, which is made of polycarbonate (GE Lexan HF 1140), has an internal volume of about 33 ml. It is filled with a filtering medium composed of multiple layers of a non-woven web of polyester fibers (about two micron diameter). The third satellite bag 4 contains a volume of storage solution for red blood cells.

Variants of the separation bag 1 may include a separation chamber 6 having an outer circular edge 7 and/or an inner circular edge 8 that are eccentric; a separation chamber 6 comprising a radial wall extending from the inner edge 8 to the outer edge 7 so that the chamber 6, instead of being annular, is C-shaped. A separation chamber 6 having any shape including an inner edge and an outer edge (the inner edge being closer to the axis of the rotor of a centrifuge than the outer edge, when the separation bag is mounted on the rotor of a centrifuge), for example the shape of a portion of annulus delimited by two lateral radial edge or a rectangular shape. In this variant, all the satellite bags may be connected to the inner edge of the separation bag.

Also, the separation bag 1 can be shaped so as to fit either on a flat support surface or on a frusto-conical support surface of the rotor of a centrifuge.

The bags and the tubes of the bag set shown in FIGS. 1 and 2 are all made of flexible plastic material appropriate to contact blood and blood components.

Figure 3:
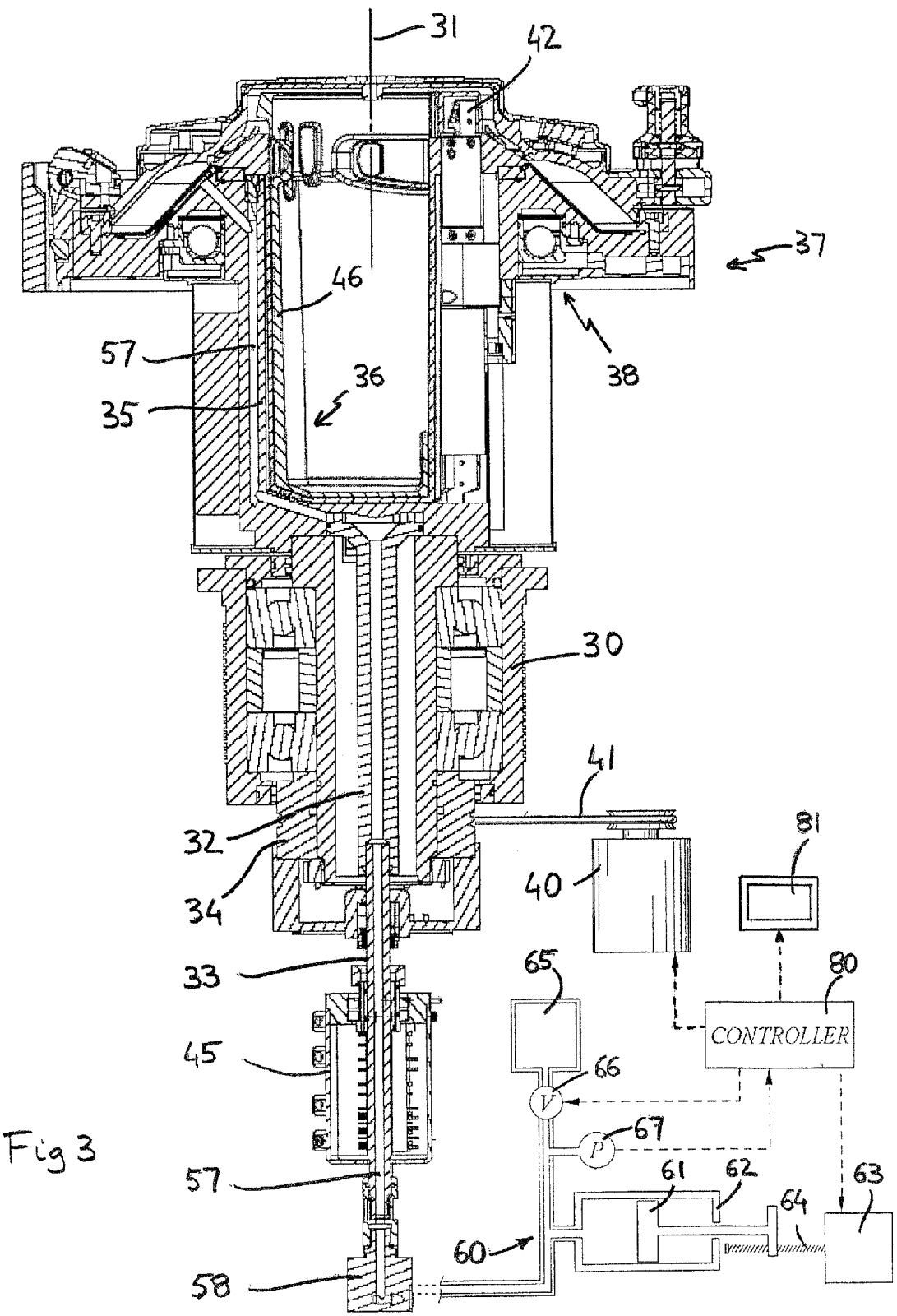
FIG. 3 is a schematic view, partly in cross-section, of a separation apparatus according to the invention.
Figure 4:
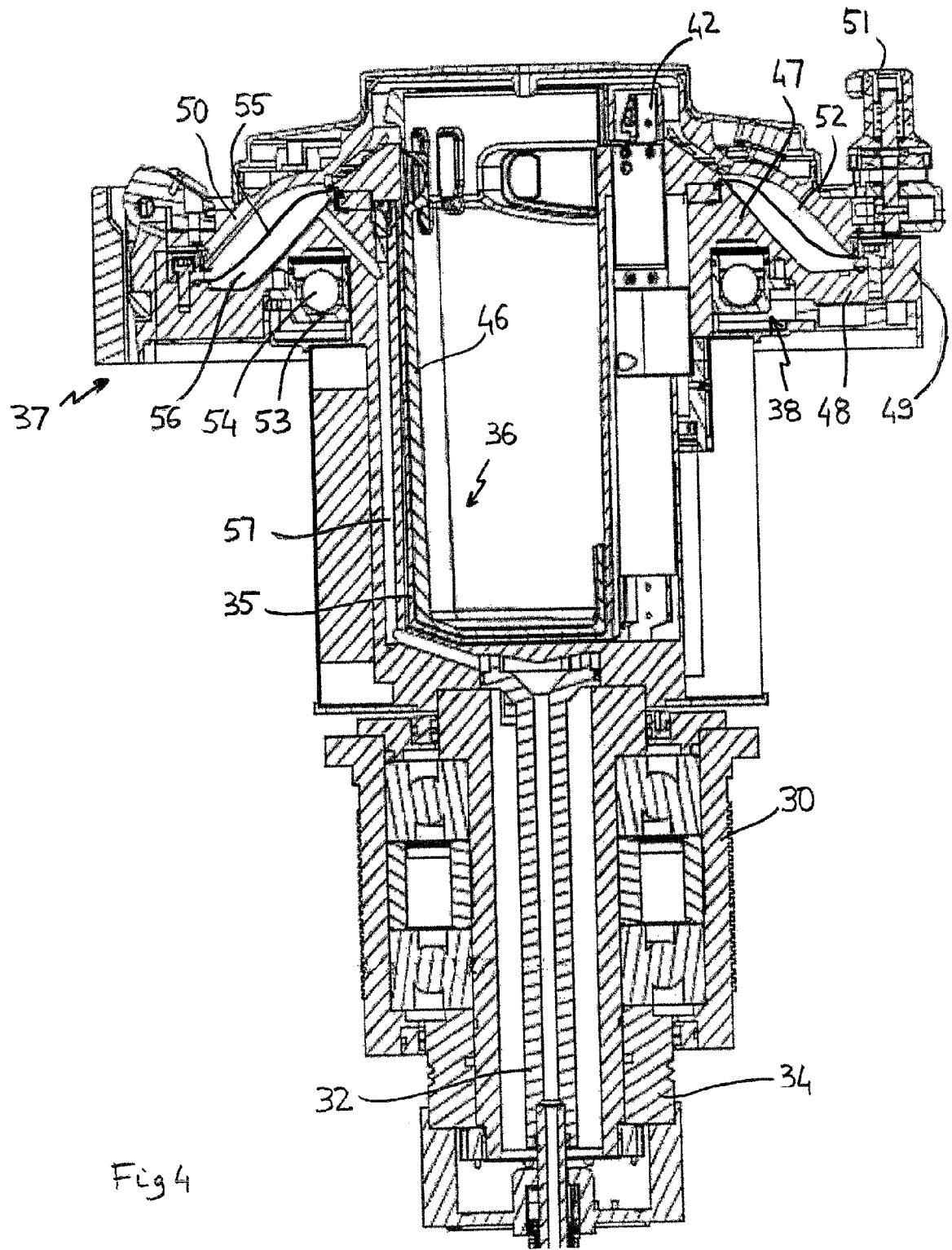
FIG. 4 is a cross-section view of the rotor of a separation apparatus according to the invention.

FIGS. 3 and 4 show an embodiment of an apparatus for separating a volume of composite liquid by centrifugation. The apparatus comprises a centrifuge adapted for receiving the set of separation bags shown in FIGS. 1 and 2, and a component transferring means for causing the transfer of separated components into the satellite bags.

The centrifuge comprises a rotor that is supported by a bearing assembly 30 allowing the rotor to rotate about a vertical central axis 31. The rotor comprises a cylindrical rotor shaft comprising a first upper portion 32 and a second lower portion 33; the upper portion 32 of the shaft extends in part through the bearing assembly 30; a pulley 34 is connected to the lower end of the upper portion 32 of the shaft; a central compartment 35 for containing satellite bags, which is connected to the rotor shaft 32, 33 at the upper end thereof; a support member 36 fitting within the central compartment 35, for supporting at least one satellite bag in a determined position within the central compartment 35; a circular turntable 37 for supporting a separation bag, which is connected to the central compartment 35 at the upper end thereof, the central axes of the rotor shaft 32, 33, the central compartment 35 and the turntable 37 coinciding with the rotation axis 31; and a balancing assembly 38, which is secured to the turntable 37.

The centrifuge further comprises a motor 40 coupled to the rotor by a belt 41 engaged in a groove of the pulley 34 so as to rotate the rotor about the central vertical axis 31.

The separation apparatus further comprises a first, second and third pinch valve members 42, 43, 44 that are mounted on the rotor for selectively blocking or allowing a flow of liquid through a flexible plastic tube, and selectively sealing and cutting a plastic tube. Each pinch valve member 42, 43, 44 comprises an elongated cylindrical body and a head having a groove that is defined by a stationary upper jaw and a lower jaw movable between an open and a closed position, the groove being dimensioned so that one of the transfer tubes 20, 25, 26 of the bag sets shown in FIGS. 1 and 2 can be snuggly engaged therein when the lower jaw is in the open position.

The elongated body contains a mechanism for moving the lower jaw and it is connected to a radio frequency generator that supplies the energy necessary for sealing and cutting a plastic tube. The pinch valve members 42, 43, 44 are mounted at the periphery of the central compartment 35 so that their longitudinal axes are coplanar, and parallel to the central axis 31 of the rotor, and their heads protrude above the rim of the central compartment 35. The position of the pinch valve members 42, 43, 44 with respect to the separation bag 1 and the transfer tubes 20, 25, 26 connected thereto when the separation bag 1 is mounted on the turntable 37 is shown in doted lines in FIG. 2. Electric power is supplied to the pinch valve members 42, 43, 44 through a slip ring array 45 that is mounted around the lower portion 33 of the rotor shaft.

The support member 36 generally comprises a portion of wall 46 that is tilted with respect to the rotation axis 31 of the rotor. A satellite bag secured by an upper portion thereof to an upper part of the tilted wall 46 is pressed against the tilted wall 46 by centrifugation forces during rotation of the rotor and a lower portion of the satellite bag is closer to the axis of rotation than an upper portion thereof. As a result, a liquid contained in the supported satellite bag drains from the supported satellite bag into the separation bag under centrifugation forces.

The turntable 37 comprises a central frusto-conical portion 47, the upper, smaller edge of which is connected to the rim of the central compartment 35, an annular flat portion 48 connected to the lower, larger edge of the frusto-conical portion 47, and an outer cylindrical flange 49 extending upwards from the outer periphery of the annular portion 48. The turntable 35 further comprises a vaulted circular lid 50 that is secured to the flange 49 by a hinge so as to pivot between an open and a closed position. The lid 50 is fitted with a lock 51 by which it can be blocked in the closed position. The lid 50 has an annular interior surface that is so shaped that, when the lid 50 is in the closed position, it defines with the frusto-conical portion 47 and the annular flat portion 48 of the turntable 37, a frusto-conical annular compartment 52 having a radial cross-section that has substantially the shape of a parallelogram. The frusto-conical annular compartment 52 (later the "separation compartment"), which has a fixed volume, is intended for containing the separation bag 1 shown in FIGS. 1 and 2.

The balancing assembly 38, which has generally the shape of a ring, is mounted on the rotor within the space that extends between the upper end of the central compartment 35 and the frusto-conical wall 47 of the turntable 37. The balancing assembly 38 comprises a ring-shaped housing 53 defining a cavity whose cross-section, along a radial plane, is generally rectangular. The balancing assembly further comprises a plurality of ponderous balls 54 having a diameter that is slightly less than the radial depth of the cavity of the housing 53. When the balls 54 are in contact with each other they occupy a sector of the housing 52 of about 180 degrees.

The component transferring means comprises a squeezing system for squeezing the separation bag within the separation compartment 52 and causing the transfer of separated components into the satellite bags. The squeezing system comprises a flexible annular diaphragm 55 that is so shaped as to line the frusto-conical portion 47 and the annular flat portion 48 of the turntable 37, to which it is secured along its smaller and larger circular edges. The squeezing system further comprises a hydraulic pumping station 60 for pumping a hydraulic liquid in and out an expandable hydraulic chamber 56 defined between the flexible diaphragm 55 and the turntable 37, via a duct 57 extending through the rotor from the lower end of the lower portion 33 of the rotor shaft to the turntable 37. The pumping station 60 comprises a piston pump having a piston 61 movable in a hydraulic cylinder 62 fluidly connected via a rotary fluid coupling 58 to the rotor duct 57. The piston 61 is actuated by a stepper motor 63 that moves a lead screw 64 linked to the piston rod 62. The stepper motor 63 can be controlled by discrete increments or steps, each step corresponding to a fraction of a turn of the axle of the motor 63; that is, also to a small linear displacement of the piston 61; that is also to a small determined volume of liquid being pumped in or out of the hydraulic chamber 56. The hydraulic cylinder 62 is also connected to a hydraulic liquid reservoir 65 having an access controlled by a valve 66 for selectively allowing the introduction or the withdrawal of hydraulic liquid into and from a hydraulic circuit including the hydraulic cylinder 62, the rotor duct 57 and the expandable hydraulic chamber 56. A pressure gauge 67 is connected to the hydraulic circuit for measuring the hydraulic pressure therein.

The separation apparatus further comprises three sensors 70, 71, 72 for detecting characteristics of the separation process occurring within a separation bag 1 when the apparatus operates. The three sensors 70, 71, 72 are embedded in the lid 50 at different distances from the rotation axis 31 of the rotor, a first sensor 70 being the closest to the rotation axis 31, a second sensor 71 being the farthest to the rotation axis 31 and a third sensor 72 occupying an intermediate position. When the lid 50 is closed, the three sensors 70, 71, 72 face the separation bag 1 as shown in FIG. 2. The first sensor 70 (later the "inner sensor") is embedded in the lid 50 so as to be positioned over the separation chamber 6 at a short distance from the end of the second transfer tube 25 connected to the second funnel-like extension 10 (plasma outlet). The inner sensor 70 is able to detect an interface gas/liquid, an interface between plasma and a platelet/mononuclear cell layer, an interface between platelet rich plasma and mononuclear cells, as well as red blood cells. The second sensor 71 (later the "outer sensor") is embedded in the lid 50 so as to be positioned over the separation chamber 6 at about two third of the width of the separation chamber from the inner edge 8 thereof, and it is offset with respect to the second funnel-like extension 10, while being closer to the end of the second transfer tube 25 than to the respective ends of the first and second transfer tubes 20, 26. The outer sensor 71 is able to detect a liquid, e.g. blood. The third sensor 72 (later the "intermediate sensor") is embedded in the lid 50 so as to be positioned over the separation chamber 6 at about one third of the width of the separation chamber from the inner edge 8 thereof, substantially on the same radius as the end of the third transfer tube 26 (platelet outlet) connected to the second funnel-like extension 10. The intermediate sensor 72 is able to detect an interface between plasma and blood cells. Each sensor 70, 71, 72 can comprise a photocell including an infra-red LED and a photo-detector. Electric power is supplied to the sensors 70, 71, 72 through the slip ring array 45.

The separation apparatus further comprises a controller 80 including a control unit (microprocessor) and a memory for providing the microprocessor with information and programmed instructions relative to various separation protocols and to the operation of the apparatus in accordance with such separation protocols. In particular, the microprocessor is programmed for receiving information relative to the centrifugation speed(s) at which the rotor is to be rotated during the various stages of a separation process, and information relative to the various transfer flow rates at which separated components are to be transferred from the separation bag 1 into the satellite bags 2, 3, 4. The information relative to the various transfer flow rates can be expressed, for example, as hydraulic liquid flow rates in the hydraulic circuit, or as rotation speeds of the stepper motor 63 of the hydraulic pumping station 60. The microprocessor is further programmed for receiving, directly or through the memory, information from the pressure gauge 67 and from the photocells 70, 71, 72 and for controlling the centrifuge motor 40, the stepper motor 63, and the pinch valve members 42, 43, 44 so as to cause the separation apparatus to operate along a selected separation protocol.

The control unit 80 is also programmed for determining and displaying on a screen 81 of the separation apparatus the actual volume of the components separated during a separation procedure, as well as the actual volume of the composite liquid (whole blood) initially contained in the separation bag 1.

An example of a first separation protocol aiming at the preparation of four blood components from a whole blood donation, namely a plasma component, a platelet component, a mononuclear cell component and a red blood cell component, is explained below.

The operation of the separation apparatus along the first separation protocol is as follows.

First Stage (First Protocol)

A bag set as shown in FIG. 1, in which the satellite bag 2 contains a volume of whole blood, is set in place in the rotor of a centrifuge (as shown in FIGS. 3, 4).

At the onset of the first stage, the first satellite bag 2 of the bag set of FIG. 1 contains a volume of anti-coagulated whole blood (usually about 500 ml). The collection tube 22 has been sealed and cut close to the first satellite bag 2. The clamp 24 on the transfer tube 27 connecting the fourth satellite bag 5 to the separation bag 1 is closed. The four satellite bags 2, 3, 4, 5 are superposed one upon another so as to form a stack that is inserted in the bag loader 36 so that the first satellite bag 2 is adjacent the tilted wall 46 of the bag loader 36. The satellite bags 2, 3, 4, 5 are secured by their upper ears to an upper part of the bag loader 36, above the tilted wall 46. In this position, they are substantially located on one side of a plane containing the rotation axis 31 of the rotor, and a lower portion of the first satellite bag 2 containing the volume of whole blood is closer to the rotation axis 31 than an upper portion thereof.

The collection bag 1 is then laid on the turntable 37 and pins (not shown) protruding on the turntable 37 around the opening of the central compartment 35 are engaged in the holes 13 of the disk-shaped connecting element 11 of the separation bag 1. The first transfer tube 20 connecting the first satellite bag 2 to the separation bag 1 is engaged in the first pinch valve member 42, the second transfer tube 25 connecting the second satellite bag 3 to the separation bag 1 is engaged in the second pinch valve member 43, and the third transfer tube 26 connecting the third satellite bag 4 to the separation bag 1 is engaged in the third pinch valve member 44. The frangible connector 21 blocking communication between the first satellite bag 2 and the separation bag 1 is broken. The lid 49 of the rotor is closed.

Second Stage (First Protocol)

The anti-coagulated whole blood contained in the first satellite bag 2 is transferred into the separation bag 1.

At the onset of the second stage, the first pinch valve member 42 is open and the second and third pinch valve members 43, 44 are closed. The rotor is set in motion by the centrifuge motor 40 and its rotation speed increases steadily until it reaches a first centrifugation speed (e.g. about 1500 RPM) that is so selected as to be high enough to cause the transfer, under centrifugation forces, of the content of the first satellite bag 2 into the separation bag 1; to be high enough to cause the whole transfer to happen in a short period of time; while, at the same time, to be low enough not to cause pressure within the first satellite bag 2 to substantially exceed a determined pressure threshold above which hemolysis would occur; and to be low enough not to generate shearing forces in the flow of blood entering the separation bag 1 that would cause hemolysis.

It has been determined that the pressure threshold above which hemolysis occurs in the satellite bag 2 is about 10 PSI, and that the maximum rotation speed at which such pressure threshold is not reached and the shearing forces in the blood flow entering the separation bag do not cause hemolysis is about 1800 RPM. At a rotation speed of about 1500 RPM, it takes about one minute for transferring about 500 ml of anticoagulated blood from the satellite bag 2 into the separation bag 1.

When the outer cell 71 detects blood, the valve member 43 controlling a flow of fluid through the second transfer tube 25 connected to the second satellite bag 3 (in which a plasma component will be later transferred) is opened for a predetermined amount of time (for example, about 30 seconds) so as to allow air to vent from the separation bag 1 when blood pours therein.

If the outer cell 71 has not detected blood within a predetermined period of time following the start of the centrifugation process, the control unit 80 causes the rotor to stop and an alarm to be emitted. This could happen in particular if the frangible connector 21 has inadvertently not been broken.

Third Stage (First Protocol)

The air present in the separation bag 1 is purged into the first satellite bag 2, in which the mononuclear cell component is to be later transferred.

At the onset of the third stage, the whole content of the first satellite bag 2 has been transferred into the separation bag 1, the first pinch valve member 42 is open, and the second and third pinch valve members 43, 44 are closed. The rotor rotates at the first rotation speed (about 1500 RPM). The pumping station 60 is actuated so as to pump hydraulic liquid at a constant flow rate (for example, about 240 ml/min) into the hydraulic chamber 56 and consequently squeeze the separation bag 1. The air present in the separation bag 1 is expelled into the first satellite bag 2 for the mononuclear cell component. After a predetermined period of time following the detection of an interface air/liquid by the inner sensor 70, the pumping station 60 is stopped and the first pinch valve member 42 is closed. A small residual volume of air remains in the separation bag 1.

Fourth Stage (First Protocol)

The blood within the separation chamber is sedimented to a desired level.

At the onset of this stage, the three pinch valve members 42, 43, 44 are closed. The speed of the rotor is increased steadily until it reaches a second, high, centrifugation speed (for example, about 3200 RPM, so-called "hard spin") at which the blood components will sediment at the desired level. The rotor is rotated at the second centrifugation speed for a predetermined period of time (for example, about 220 seconds), which is selected so that, whatever the hematocrit of the whole blood initially transferred in the separation chamber 1, the blood sediments therein at the end of the predetermined period to a point where the hematocrit of the outer annular red blood cell layer is about 90 and the inner annular plasma layer is substantially devoid of cells. In more detail, at the outcome of this sedimentation stage, the separation bag 1 exhibits four layers: a first inner layer mainly comprising plasma, a second intermediate layer mainly comprising platelets, a third intermediate layer mainly comprising white blood cells (lymphocytes, monocytes and granulocytes), and a fourth outer layer mainly comprising red blood cells, wherein the third and fourth layers partially overlap (the granulocytes are in part embedded in the fourth layer).

Fifth Stage (First Protocol)

A plasma component is transferred into the second satellite bag 3.

At the onset of this stage, the three pinch valve members 42, 43, 44 are closed. The rotor is rotated at the same high centrifugation speed as in the sedimentation stage. After a predetermined period of time after the intermediate sensor 72 has detected the outwards moving plasma/blood cell interface, which can happen before the end of the predetermined sedimentation period, the second pinch valve member 43 controlling the access to the second satellite bag 3 is opened and the pumping station 60 is actuated so as to pump hydraulic liquid at a constant flow rate (for example, about 220 ml/min) into the hydraulic chamber 56. The expanding hydraulic chamber 56 squeezes the separation bag 1 and causes the transfer of the residual volume of air and plasma into the second satellite bag 3. The pumping station 60 is stopped and the second pinch valve member 43 is closed after a predetermined period of time has elapsed following the detection of the inward moving plasma/blood cell interface by the intermediate sensor 72. At the end of this stage, a first, larger, fraction of the total volume of plasma is in the second satellite bag 3, whereas a second, smaller, fraction of the total volume of plasma remains in the separation bag 1.

The transfer flow rate of the plasma component (which is directly related to the flow rate of the hydraulic fluid) is selected to be as high as possible without disturbing the platelet layer so as to avoid contaminating the plasma component with platelets.

The control unit 80 determines the volume of plasma that has been transferred into the second satellite bag 3 as follows. First, it determines when plasma actually starts pouring into the second satellite bag 3, after the residual amount of air present in the separation bag has been evacuated in the second satellite bag 3. Second, it counts the number of steps performed by the stepper motor 63 between the time plasma actually starts pouring into the second satellite bag 3, and the time the pumping station 60 stops pumping hydraulic liquid into the hydraulic chamber 56 after the intermediate sensor 72 has detected an interface plasma/blood cells. Finally, the control unit 80 calculates, from the counted number of steps and the determined small volume associated to one step, the total volume of hydraulic liquid pumped into the hydraulic chamber 56 during this stage, which corresponds to the volume of plasma in the second satellite bag 3.

The control unit 80 determines when plasma actually starts pouring into the second satellite bag 3 by continuously recording discrete successive values of the pressure of the hydraulic liquid as measured by the pressure sensor 67, and simultaneously analyzing how the pressure evolves, for example by calculating, each time a new pressure value is recorded, from the average of the last four measured values the slope of a curve representing the evolution of the pressure with respect to time, and by comparing the series of slopes so calculated. The control unit 80 determines the point in time at which plasma start pouring into the second satellite bag as corresponding to a drastic turning point between a first phase of steadily increasing pressure and a second phase of substantially constant pressure.

The control unit 80 can be programmed to cause the actual volume of plasma in the second satellite bag 3, once determined, to be displayed on the screen 81.

The control unit 80 also determines the volume of anticoagulated whole blood that has been transferred into the separation bag 1 during the third stage, first, by counting the number of steps performed by the stepper motor 63 between the time the pumping station 60 starts pumping hydraulic fluid into the hydraulic chamber 56 at the third stage (transfer of air into the first satellite bag 2), and the time when plasma actually starts pouring into the second satellite bag 3, as determined above; and second, by the control unit 80 calculating from the counted number of steps and the determined small volume associated to one step, the total volume of hydraulic liquid pumped into the hydraulic chamber 56 until the separation compartment 52 does not contain air anymore; and finally, by the control unit 80 calculating the volume of anti-coagulated blood that is in the separation chamber 1, by subtracting the volume of hydraulic liquid so calculated from a fixed volume, stored in the memory of the control units 80. This fixed volume corresponds to the fixed volume of the separation compartment 52, minus the volume of the diaphragm 55, minus the volume of the two superposed rings of plastic sheets delimiting the separation chamber 6, and minus a fixed residual volume of hydraulic liquid in the hydraulic chamber 56.

The control unit 80 can be programmed to cause the actual volume of anti-coagulated blood in the separation bag 1, once determined, to be displayed on the screen 81.

Sixth Stage (First Protocol)

A platelet component is prepared in the separation bag 1.

First variant: the third pinch valve member 44 controlling access to the third satellite bag 4 is open, and the first and second pinch valve members 42, 43 are closed The rotation speed of the rotor is rapidly decreased from the second centrifugation speed to a third centrifugation speed (for example, from about 3200 RPM to about 2000 RPM, within about 10 seconds) so as to form an intermediate component resulting from the suspension of the platelets into the second fraction of the plasma, whereas the red blood cell layer and the suspended platelet layer remains substantially separated.

Second variant: the three pinch valve members 42, 43, 44 are closed. The rotation speed of the rotor is rapidly decreased from the second centrifugation speed to a third centrifugation speed (for example, from about 3200 RPM to about 1000 RPM, within about 20 seconds) so as to mix red blood cells, the platelets and the second portion of the plasma. The rotation speed of the rotor is then increased from the third centrifugation speed to a fourth centrifugation speed, lower that the first centrifugation speed (for example, from about 1000 RPM to about 2500 RPM), so as to separate in the separation bag 1 a red blood cell component and a platelet component comprising a suspension of platelets in plasma.

Seventh Stage (First Protocol)

The platelet component is transferred into the fourth satellite bag 3.

The third pinch valve member 44 controlling the access to the third satellite bag 4 is open and the first and second pinch valve members 42, 43 are closed. The rotor is rotated at the third centrifugation speed (for example, about 2000 RPM, if the preceding stage is the first variant of the sixth stage) or at the fourth rotation speed (for example, about 2500 RPM, if the preceding stage is the second variant of the sixth stage). The pumping station 60 is actuated so as to pump hydraulic liquid at a first flow rate into the hydraulic chamber 56 and consequently squeeze the separation bag 1 and cause the transfer of the platelet component into the third satellite bag 4. The first flow rate (for example, about 140 ml/min) is substantially lower than the flow rate (for example, about 220 ml/min) at which the plasma component is transferred into the second satellite bag 3 in the fifth stage. The first transfer flow rate of the platelet component, (which is directly related to the first flow rate of the hydraulic fluid), is selected to be high enough for preventing the suspended platelets from sedimenting, without, at the same time, triggering the activation of the platelets.

When the inner sensor 70 detects an interface between the suspended platelets and mononuclear/red blood cells, the pumping station 60 is actuated so as to pump hydraulic liquid into the hydraulic chamber 56 at a second flow rate, (for example 40 ml/min), that is substantially lower than the first flow rate, in order to prevent the contamination of the platelet component by mononuclear/red blood cells.

When a predetermined volume of hydraulic liquid has been pumped into the hydraulic chamber 56 at the second flow rate, the pumping station 60 is actuated so as to pump hydraulic liquid at a third flow rate, (for example, about 20 ml/min), that is lower than the second flow rate. When a predetermined volume of hydraulic liquid has been pumped into the hydraulic chamber 56 at the third flow rate, the pumping station 60 is stopped.

The control unit 80 determines the volume of the platelet component that has been transferred into the third satellite bag in the following manner it first counts the number of steps performed by the stepper motor 63 between the time the pumping station 60 starts pumping hydraulic fluid into the hydraulic chamber 56 following the opening of the third pinch valve member 44, and the time the pumping station 60 stops doing so after the inner sensor 70 has detected the interface between the suspended platelets and the mononuclear/red blood cells; second, the control unit 80 calculates, from the counted number of steps and the determined small volume associated to one step, the total volume of hydraulic liquid pumped into the hydraulic chamber 56 during this stage, which corresponds to the volume of the platelet component in the third satellite bag 4.

The control unit 80 can be programmed to cause the actual volume of the platelet component in the third satellite bag 4, once determined, to be displayed on the screen 81.

Eighth Stage (First Protocol)

A mononuclear cell component is transferred into the first satellite bag 2.

The eighth stage can start as soon as the third pinch valve member 44 is closed at the end of the seventh stage. At the onset of this eighth stage, the three pinch valve members 42, 43, 44 are closed. The rotor is rotated at the same centrifugation speed as previously. The first pinch valve member 42 controlling the access to the first satellite bag 2 is opened and the pumping system 60 is actuated so as to pump hydraulic liquid at a constant flow rate, (for example, about 140 ml/min), into the hydraulic chamber 56. The expanding hydraulic chamber 56 squeezes the separation bag 1 and causes the transfer, into the first satellite bag 2, of a mononuclear cells component comprising lymphocytes, monocytes, a small amount of red blood cells, as well a residual volume of platelet rich plasma. The pumping system 60 is stopped and the first pinch valve member 42 is closed after a predetermined volume, (e.g. between 10 and 15 ml), has been transferred into the first satellite bag 2.

The control unit 80 determines the actual volume of the mononuclear cell component in the first satellite bag 2 by adding the volume of the mononuclear cell component actually transferred into the first satellite bag 2, which volume corresponds to the number of steps performed by the stepper motor between the opening and the closing of the first pinch valve member 42, to an empirically determined volume of whole blood remaining in the first satellite bag 2, which is stored in the memory of the control unit.

The control unit 80 can be programmed to cause the actual volume of the mononuclear cell component in the first satellite bag 2, once determined, to be displayed on the screen 81.

The control unit 80 determines the volume of red blood cells remaining in the separation bag 1 by subtracting, from the previously determined volume of anti-coagulated whole blood, the previously determined volumes of plasma component, platelet component, and mononuclear cell component.

The control unit 80 can also determine the volume of red blood cells in the fourth satellite bag 5, which will result from the actual subsequent transfer of red blood cells from the separation bag 1 into the fourth satellite bag 5 at the outcome of the tenth stage of the first separation protocol. The control unit 80 calculates the volume of red blood cells by subtracting, from the previously determined volume of anti-coagulated whole blood, the previously determined volumes of plasma component, platelet component, mononuclear cell component, and the internal volume of the leuko-reduction filter 28, and adding to the result the known volume of red blood cell storage solution contained in the fourth satellite bag 5.

The control unit 80 can be programmed to cause either one of the actual volume of the red blood cell component in the separation bag 1 and the actual volume of the red blood cell component in the fourth satellite bag 5, or both, once determined, to be displayed on the screen 81.

Ninth Stage (First Protocol)

The centrifugation process is ended.

The rotation speed of the rotor is decreased until the rotor stops, the pumping system 60 is actuated so as to pump the hydraulic liquid from the hydraulic chamber 56 at a high flow rate, (for example, about 800 ml/min), until the hydraulic chamber 56 is substantially empty, and the pinch valve members 42, 43, 44 are actuated so as to seal and cut the transfer tubes 20, 25, 26. Red blood cells remain in the separation bag 1.

Tenth Stage (First Protocol)

A red blood cell component is transferred into the fourth satellite bag 5.

The lid 50 of the rotor is opened and the separation bag 1 connected to the fourth satellite bag 5 is removed therefrom. The clamp 24 on the transfer tube 27 is opened. The frangible connector 29 blocking communication between the fourth satellite bag 5 and the leuko-reduction filter 28 is broken. The storage solution contained in the fourth satellite bag 5 is allowed to flow by gravity through the filter 28 and into the separation bag 1 where it is mixed with the red blood cells so as to lower the viscosity thereof. The content of the separation bag 1 is then allowed to flow by gravity through the filter 28 and into the fourth satellite bag 5. The white blood cells (granulocytes and residual monocytes and lymphocytes) are trapped by the filter 28, so that the ultimate packed red blood cell component in the fourth satellite bag 5 is substantially devoid from white blood cells and meets the standard of the AABB (American Association of Blood Banks), which is less than $5 \times 10^6$ white blood cells per packed red blood cell component.

The above apparatus can be programmed to carry out other separation protocols, for example for carrying out a second separation protocol for separating three components, namely a plasma component, a "buffy coat" component comprising plasma, platelets, white blood cells and red blood cells, and a red blood cell component, or a third separation protocol for separating two components, namely a platelet rich plasma component and a red blood cell component.

A set of bags as shown in FIG. 1, without a third satellite bag (for platelets), is used for carrying out the second protocol. The main steps of the second protocol are as follows: the whole blood is transferred from the first satellite bag 2 into the separation bag 1; after a hard spin sedimentation step (3200 RPM), most of the plasma is transferred into the second satellite bag 3 and a "buffy coat" component of predetermined volume is transferred into the first satellite bag 2; and the red blood cells are transferred by gravity into a red blood cell satellite bag 5. The control unit 80 determines the volume of anti-coagulated whole blood, of the plasma component, the "buffy coat" component, and a red blood cell component as explained above with respect to the first protocol, (the "buffy coat" component corresponding to the mononuclear cell component).

A set of bags as shown in FIG. 1, without a third satellite bag (for platelets), is used for carrying out the third protocol. The main steps of the third protocol are as follows: the whole blood is transferred into the separation bag 1 from the first satellite bag 2 (which is not re-used later); after a soft spin sedimentation step (2000 RPM), a platelet rich plasma component is transferred into the second satellite bag 3; and the red blood cells are finally transferred by gravity into a red blood cell satellite bag 5. The control unit 80 determines the volume of anti-coagulated whole blood, of the platelet rich plasma component, and of the red blood cell component as explained above with respect to the first protocol, (the platelet rich plasma component corresponding to the plasma component).

As mentioned above, the various actual volume values determined by the control unit 80 can be selectively displayed on the screen 81 of the separation apparatus. They are also stored in the memory of the control unit to be later printed on the satellite bags. This data can also be transferred to a database collecting separation data from multiple separation apparatuses and protocols so as to serve for statistical analyses.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. A method for separating a composite liquid into at least a first component and a second component, comprising:
   centrifuging a separation bag contained in a fixed volume separation compartment, the separation bag comprising a first volume and containing a content comprising a second volume of the composite liquid and a residual volume of a gas so as to cause the sedimentation of at least the first component and the second component in the separation bag, wherein the first volume is different from the second volume;
   displacing a volume of a hydraulic fluid against the separation bag comprising:
      applying a pressure onto the separation bag;
      causing a transfer of the volume of the gas contained in the separation bag into at least one component bag; and
      causing a transfer of a first fraction of the content of the separation bag into a first component bag connected to the separation bag;
   determining a volume of the hydraulic fluid being displaced so as to cause the transfer of the gas until the first fraction of the content of the separation bag starts to transfer into the first component bag; and
   determining the second volume of the composite liquid in the separation bag from the fixed volume of the separation compartment, and the determined volume of the hydraulic fluid being displaced so as to cause the transfer of the gas until the first fraction of the content starts to transfer into the first component bag.

2. A method according to claim 1, wherein applying a pressure onto the separation bag and causing the transfer of the first fraction of the content of the separation bag into the first component bag comprises:
causing the residual volume of the gas and the first fraction of the content to flow into the first component bag, wherein the first fraction of the content comprises a first fraction of the first component; and
stopping the flow of the first component into the first component bag when at least the first fraction of the first component has been transferred into the first component bag.

3. A method according to claim 2, further comprising:
determining when the first component starts pouring into the first component bag after the residual volume of the gas has been transferred therein, and determining an actual volume of the first fraction of the first component transferred into the first component bag from the volume being transferred between the first component starting pouring into the first component bag and the first component stopping flowing into the first component bag.

4. A method according to claim 3, wherein determining when the first component starts pouring into the first component bag comprises:
monitoring an evolution of the pressure applied onto the separation bag; and
determining from a change in the pressure applied onto the separation bag when the first fraction of the first component starts pouring into the first component bag.

5. A method according to claim 4, wherein the change in pressure corresponds to the pressure becoming substantially constant after having substantially steadily risen during the transfer of the residual volume of the gas into the first component bag.

6. A method according to claim 4, wherein applying a pressure onto the separation bag comprises pumping the hydraulic fluid into the separation compartment comprising:
pumping the hydraulic fluid in increments of a determined discrete volume; and
determining the actual volume of the first fraction of the first component transferred into the first component bag comprises counting a number of increments between the first component starting pouring into the first component bag and the first component stopping flow into the first component bag.

7. A method according to claim 2, further comprising detecting an interface between the first component and the second component in the separation bag at a distance from a centrifugation axis, wherein the flow of the first component into the first component bag is stopped after the interface is detected.

8. A method according to claim 2, wherein displacing the volume of the hydraulic fluid against the separation bag comprises:
pumping the hydraulic fluid, in increments of a determined discrete volume, into the separation compartment in which the separation bag is enclosed; and
determining the second volume of the composite liquid in the separation bag comprises counting a number of increments between the hydraulic fluid starting flowing into the separation compartment and the first component starting pouring into the first component bag.

9. A method according to claim 2, further comprising determining an actual volume of the second component in the separation bag from at least the determined second volume of the composite liquid in the separation bag, and an actual volume of the first component transferred into the first component bag.

10. A method according to claim 1, further comprising:
causing, by the centrifuging of the separation bag containing the second volume of the composite liquid, the sedimentation of an intermediate component in the separation bag;
detecting an interface between the first component and the intermediate component in the separation bag at a distance from a centrifugation axis;
stopping the transfer of the first fraction of the content into the first component bag connected to the separation bag after the interface is detected, wherein the first fraction of the content comprises a first fraction of the first component;
causing a third component to flow into a third component bag connected to the separation bag when the first fraction of the first component has been transferred into the first component bag, wherein the third component comprises a fraction of the second component, the intermediate component, and a second fraction of the first component remaining in the separation bag;
stopping the flow of the third component into the third component bag when a volume thereof has been transferred into the third component bag; and
determining an actual volume of the third component in the third component bag.

11. A method according to claim 10, further comprising:
initially transferring the second volume of the composite liquid into the separation bag from a composite liquid bag connected to the separation bag, wherein a residual volume of the composite liquid remains in the composite liquid bag, and wherein the residual volume has a known value; and
using the composite liquid bag as the third component bag.

12. A method according to claim 11, wherein determining the actual volume of the third component in the third component bag comprises determining the volume of the third component caused to flow into the third component bag, wherein the actual volume of the third component in the composite liquid bag is determined from at least the residual volume of the composite liquid and the determined volume of the third component caused to flow into the composite liquid bag.

13. A method according to claim 10, wherein the composite liquid comprises whole blood, the first component comprises plasma, the second component comprises red blood cells, and the intermediate component comprises platelets.

* * * * *